United States Patent [19]

Smith et al.

[11] Patent Number: 4,745,051
[45] Date of Patent: May 17, 1988

[54] METHOD FOR PRODUCING A RECOMBINANT BACULOVIRUS EXPRESSION VECTOR

[75] Inventors: Gale E. Smith; Max D. Summers, both of Bryan, Tex.

[73] Assignee: The Texas A&M University System, College Station, Tex.

[21] Appl. No.: 498,858

[22] Filed: May 27, 1983

[51] Int. Cl.[4] .................. C12P 21/00; C12P 19/34; C12N 15/00; C12N 1/00; C12N 7/00; C07H 21/04

[52] U.S. Cl. .................. 435/68; 435/172.1; 435/172.3; 435/91; 435/320; 435/235; 435/243; 935/32; 935/57; 935/70; 536/27

[58] Field of Search .................. 435/68, 70, 91, 172.3, 435/317, 235, 239, 240, 241, 253, 172.1, 240.1, 240.2, 240.25, 243, 320; 935/32, 57, 70; 536/27

[56] References Cited

U.S. PATENT DOCUMENTS 4,322,499 3/1982 Baxter .................. 435/317

OTHER PUBLICATIONS

Miller: "A Virus Vector for Genetic Engineering in Invertebrates", pp. 203–224, in N. Panapoulous (ed.), *Genetic Engineering in the Plant Sciences*, Praeger Pub., New York, (1981).

Miller: J. Supramol. Struct. Cell. Biochem., (Suppl. 5), 441, (1981).

Miller et al.: in *Genetic Engineering in Eukaryotes*, Lurquin et al. (ed.), Plenum Press, New York, (1982), pp. 89–97.

Smith et al.: J. Virol., 33, 311, (1980).

Summers, in "The Atlas of Insects and Plant Viruses," 3–27, Academic Press, New York, (1977).

Smith, et al., "Analysis of Baculovirus Genemes with Restriction Endonucleases," Virology, 89:517–27, (1978).

Smith, et al., "Restriction Maps of Five *Autographa californica* MNPV Variants, *Trichoplusia ni* MNPV, and *Galleria mellonella* MNPV DNAs with Endonucleases SmaI, KnpI, BamHI, SacI, XhoI, and EcoRI," J. Virol., 30:828–838, (1979).

Summers, in "Biological Control", (published in the Proceedings of a Joint U.S.—Chinese Academy of Sciences Symposium", (Sep. 1982).

Adang, et al., "Molecular Cloning of DNA Complementary to mRNA of the Baculovirus *Antographa californica* Nuclear Polyhedrosis Virus: Location and Gene Products of RNA Transcripts Found Late in Infection," J. Virol., 44:782–793, (Dec. 1982).

Smith, et al., "Physical Analysis of *Autographa californica* Nuclear Polyhedrosis Virus Transcripts for Polyhedrin and 10,000-Molecular-Weight Protein," J. Virol., 45:215–225, (Jan. 1983).

Miller et al., "Bacterial, Viral, and Fungal Insecticides," Science, 219:715–721, (Feb. 1983).

Miller, et al., "A Temperature-Sensitive Mutant of the Baculovirus *Autographa californica* Nuclear Polyhedrosis Virus Defective in an Early Function Required for Further Gene Expression," Virology, 126:376–380, (Apr. 1983).

Smith, et al., "Molecular Engineering of the *Autographa californica* Nuclear Polyhedrosis Virus Genome: Deletion Mutations Within the Polyhedrin Gene," J. Virol., 46:584–593, (May 1983).

(List continued on next page.)

Primary Examiner—James Martinell
Attorney, Agent, or Firm—Arnold, White & Durkee

[57] ABSTRACT

A method for producing a recombinant baculovirus expression vector, capable of expression of a selected gene in a host insect cell, is disclosed. The preferred method involves cleaving baculovirus DNA to produce a DNA fragment comprising a polyhedrin gene or portion thereof, including a polyhedrin promoter. A recombinant shuttle vector is prepared by inserting said DNA fragment into a cloning vehicle and thereafter inserting a selected gene into the thus modified cloning vehicle such that it is under the transcriptional control of the polyhedrin promoter. The recombinant shuttle vector is contacted with a baculovirus DNA so as to effect recombination and incorporation of the selected gene into the baculovirus genome.

29 Claims, 6 Drawing Sheets

OTHER PUBLICATIONS

Smith, et al., "Production of Human Beta$_1$ Interferon in Insect Cells Infected with a Baculovirus Expression Vector," Mol. Cell. Biol., 3:2156–2165, (Dec. 1983).

Pennock, et al., "Strong and Regulated Expression of *Escherichia coli* B–Galactosidase in Insect Cells with a Baculovirus Vector," Mol. Cell. Biol., 4:399–406, (Mar. 1984).

Mocarski, et al., "Molecular Engineering of the Herpes Simplex Virus Genome: Insertion of a Second L–S Junction into the Genome Causes Additional Genome Inversions," Cell, 22:243–255, (1980).

Maniatis, et al., *Molecular Cloning: A Laboratory Manual,* Cold Spring Harbor Laboratory, (1982), pp. 88–94, 100–102, 104, 105, 115, 125, 126, 133–135, 138–140, 249–251, 446–449, 458, 459, 461, and 462.

Brinster, et al., "Induction of Foreign Genes in Animals," Trends in Biochemical Sci., 7:438–440, (1982).

Mackett, et al., "Vaccinia Virus: A Selectable Eukaryotic Cloning and Expression Vector," Proc. Natl. Acad. Sci., U.S.A., 79:7415–7419, (1982).

Smith, et al., "Site–Directed Mutagenesis," Trends in Biochemical Sci., 7:440–442, (Dec. 1982).

Miyanohara, et al., "Expression of Hepatitis B Surface Antigen Gene in Yeast," Proc. Natl. Acad. Sci., U.S.A., 80:1–5, (Jan. 1983).

Hitzeman, et al., "Secretion of Human Interferons by Yeast," Science, 219:620–625, (Feb. 1983).

Demain, et al., "New Applications of Microbial Products," Science, 219:709–714, (Feb. 1983).

Dierks, et al., "Three Regions Upstream from the Cap Site are Required for Efficient and Accurate Transcription of the Rabbit B–Globin Gene in Mouse 3T6 Cells," Cell, 32:695–706, (Mar. 1983).

Miller, "Interferon Roundup: Y–Form and Yeast," Science News, 123:138, (1983).

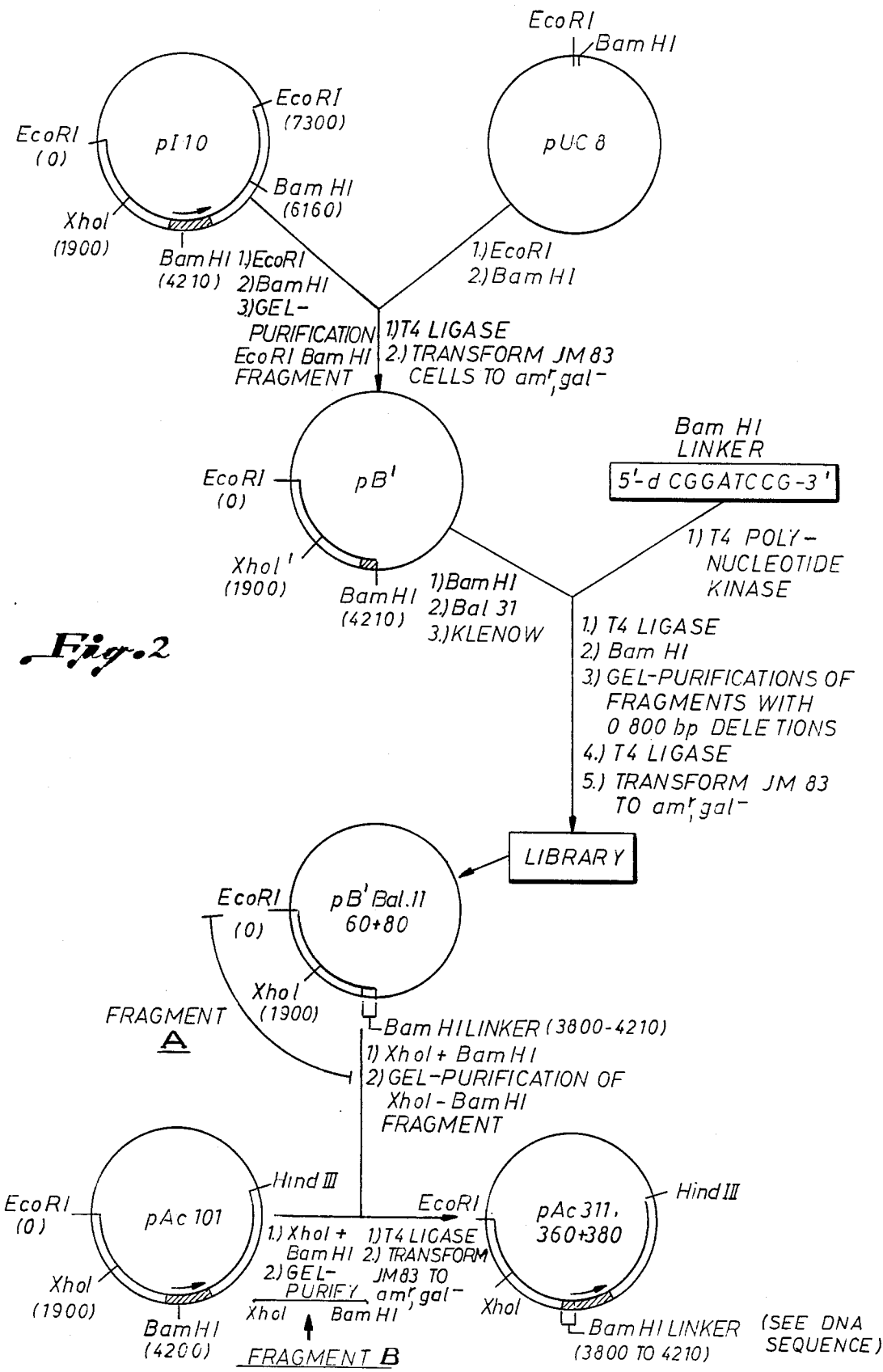

Fig. 3

```
GGTCTG CGAGCA GTT GTT TGT TGT TAA AAATAA CAG CCATTG TAATGA GACGGCACAAACT AAT AATCAC AAACTG GAAAATGTC TAT CAATAT ATA GTT
-197                                                      -141            -127                        -109
                                              pAc380→                                          pAc373→
GCT GAT ATC ATGGAGA TAATT AAAAT GATA ACC ATC TCGC AAA TAAAAT AAGTATTTT ACTGTTTTC GTA ACAGTT TTGTAA TAA AAAAACCTA TAAAT
 -98 EcoRV                        -77                 -57
                                                   *****
         pro asp tyr ser tyr arg pro thr ile gly arg thr tyr val tyr asp asn lys tyr tyr lys asn leu gly
    ATG  CCG GAT TAT TCA TAC CGT CCC ACC ATC GGG CGT ACC TAC GTG TAC GAC AAC AAG TAC TAC AAA AAT TTA GGT
    +1   Mspl                                  pAc311
                                                    pAc360→ ala val ile lys asn ala glu val ala lys arg lys lys his phe ala glu his glu ile glu ala thr glu glu ala thr leu asp pro leu
    GCC GTT ATC AAG AAC GCT GAA GTT GCT AAG CGC AAG AAG CAC TTC GCC GAA CAT GAG ATC GAA GAG GCT ACC CTC GAC CCC CTA
     76                                                                                       Sau3A                    Taql
                                                                                                    pAc101→
    asp asn tyr leu val ala glu asp pro phe leu gly pro phe leu gly pro gly lys asn gln lys leu thr leu phe lys glu ile
    GAC AAC TAC CTA GTG GCT GAG GAT CCT TTC CTG GGA CCC GGC AAG AAC CAA AAA CTC ACT CTC TTC AAG GAA ATC
    151                              BamHI                         Mspl
                                     Sau3A arg asn val lys pro asp thr met lys leu val val gly trp lys gly lys glu phe tyr arg glu thr trp thr
    CGT AAT GTT AAA CCC GAC ACG ATG AAG CTT GTC GTT GGA TGG AAA GGA AAA GAG TTC TAC AGG GAA ACT TGG ACC
    226                             HindIII
```

AUTOGRAPHA CALIFORNICA
MNPV-IFN-β RECOMBINANT

Fig. 5

METHOD FOR PRODUCING A RECOMBINANT BACULOVIRUS EXPRESSION VECTOR

The Government may have rights in this invention pursuant to a funding agreement with the National Institutes of Health, Grant No. 5 RO1 AI14755.

BACKGROUND OF THE INVENTION

This invention relates to a method for producing a recombinant viral expression vector. More particularly, this invention relates to a method for incorporating a selected gene coupled with a baculovirus polyhedrin promoter into a baculovirus genome to produce a recombinant baculovirus expression vector capable of expression of the selected gene in a host insect cell.

Recent advances in recombinant DNA technology have facilitated the isolation of specific genes or parts thereof and their transfer to bacteria, yeast or viruses. The transferred or modified gene(s) is replicated and propagated as the transformed microorganisms or viruses replicate and, as a result, the genetically altered recombinant may then have the capacity to produce the gene product for which the transferred gene sequences encode.

The transfer and expression of genes, or portions thereof, between viruses, eukaryotes and prokaryotes is possible because the DNA of all living organisms is chemically similar in that it is composed of the same four nucleotides. The basic differences reside in the sequence of the nucleotides in the genome of the organism. The nucleotide sequences are arranged in codons (nucleotide triplets) which code for specific amino acids with the coding relationship between amino acid sequence and nucleotide sequence being essentially the same for all organisms.

The DNA is organized into genes which are comprised of protein encoding genes (i.e., "structural genes") and control regions (usually referred to as the "promoter") that mediate initiation of expression of the structural gene. In general, the enzyme RNA polymerase is activated by the promoter such that as it travels along the structural gene, it transcribes encoded information into a messenger ribonucleic acid (mRNA). The mRNA contains recognition sequences, signals for ribosome binding, and signals for translational start and stop. Recent advances in the genetic analysis of the role of important transcriptional signals in the promoter regions of genes (which are usually described as the 5' flanking region of protein coding genes) have facilitated the ability to selectively remove or alter DNA sequences to study their function and role in expression, and to remove certain of these sequences to study their function in heterologous biological systems such as a host-vector system.

Eukaryotic promoters are usually characterized by two conserved sequences of nucleotides whose locations and structural similarity to prokaryotic promoter sequences (Breathnach & Chambon, *Ann. Rev. Biochem.* 50, 349–383 (1981)) suggest involvement in the promotion of transcription. The first is a sequence rich in the nucleic acids adenine and thymine (the Goldberg-Hogness, "TATA," or "ATA" box) which is located 20–30 base pairs upstream from the RNA initiation site (the cap site which is the transcriptional start site for the mRNA) and is characterized by a concensus sequence (5'-TATAA-ATA-3'). The second region is the CCAAT box (Efstratiadis, et al., *Cell* 21, 653–668 (1980)), which is located 70–90 base pairs upstream from the cap site of some genes and has the canonical sequence 5'-GG(C/T)CAATCT-3' (Benoist, et al., *Nucleic Acids Res.* 8, 127–142 (1980)). The development of techniques for removing and altering these sequences (Nathan and Smith, *Ann. Rev. Biochem.* 44, 273–293 (1975); Weber, et al.*In*: D. D. Brown and C. F. Fox (Eds.), Developmental Biology Using Purified Genes, ICN-UCLA Symposium on Molecular and Cellular Biology (New York, Academic Press, 1981) pp. 367–385) has made it possible to separate genes from their promoter regions or portions thereof in order to study their function in heterologous biological systems.

This has been accomplished by the use of restriction endonuclease enzymes and cloning to produce recombinant DNA molecules and the controlled removal or alteration of the cloned nucleotide sequences by in vitro or site-specific mutagenesis. Restriction endonucleases are hydrolytic enzymes capable of catalyzing the site-specific cleavage of DNA molecules. The site of restriction enzyme activity is determined by the presence of a specific nucleotide sequence and is termed the recognition site for a given restriction endonuclease. Many restriction enzymes have been isolated and classified according to their recognition site. Some restriction endonucleases hydrolyze the phospho-diester bonds on both DNA strands at the same point to produce blunt ends, while others hydrolyze bonds which are separated by a few nucleotides from each other to produce free single-stranded regions at the end of each DNA molecule. These single-stranded ends are self-complementary and may be used to rejoin the hydrolyzed DNA or another or heterologous DNA sequences with the same complementary single-stranded sequences.

Restriction sites are relatively rare, however the general use of restriction endonucleases has been greatly improved by the availability of chemically synthesized double-stranded oligonucleotides containing the desired restriction site sequence. Virtually any naturally occurring, cloned, genetically altered or chemically synthesized segment of DNA can be coupled to any other segment by attaching an oligonucleotide containing the appropriate recognition sites to the ends of the DNA molecule. Subjecting this product to the hydrolytic action of the appropriate restriction endonuclease produces the requisite complementary ends for coupling the DNA molecules.

Recognition sites for specific restriction enzymes are usually randomly distributed, therefore, cleavage by a restriction enzyme may occur between adjacent codons, within a codon or at some random site in the gene. While there are many possible variations on this scheme, it is important to note that techniques are available for inserting DNA sequences in the proper location and orientation with respect to a promoter region to allow expression of those sequences.

Potentially, any DNA sequence can be cloned by inserting a foreign DNA sequence into a cloning vehicle or vector molecule to construct an artificial recombinant molecule or composite sometimes called a chimera or hybrid. For most purposes, the cloning vehicle utilized is a duplex extrachromosomal DNA sequence comprising an intact replicon such that the recombinant molecule can be replicated when placed into bacteria or yeast by transformation. Cloning vehicles commonly in use are derived from viruses and plasmids associated with bacteria and yeast.

Recent advances in biochemistry and recombinant DNA technology have led to the construction of cloning vehicles or vectors containing "heterologous" DNA. The term "heterologous" refers to DNA that codes for polypeptides ordinarily not produced by the cell susceptible to transformation but which are incorporated into the genome of the cell(s) when the recombinant is introduced into the cell(s) by transformation. The transformant is thereafter isolated and cultured, thus obtaining large populations of the cell(s) which include copies of the foreign gene which may or may not be expressed in that particular cell. These populations provide a renewable source of the recombinant for further manipulations, modifications and transfer to other vectors.

Once the gene or desirable portions thereof have been cloned and or biochemically modified in the desired manner or other biochemically modified or genomic genes have been inserted in such a manner as to facilitate their expression, they are then transferred to an expression vector. Because of the nature of the genetic code, the cloned or hybrid gene or portions thereof will direct the production of the amino acid sequences for which it codes. The general techniques for constructing expression vectors with cloned genes located in the proper relationship to promoter regions are described by B. Polisky, et al., *Proc. Natl. Acad. Sci. U.S.A.* 73, 3900 (1976), K. Itakura, et al., *Science* 198, 1056–1063 (1977), L. Villa-Komaroff, et al., *Proc. Natl. Acad. Sci. U.S.A.* 75, 3727–3731 (1978) and others.

The term "expression" may be characterized in the following manner. Even in relatively simple prokaryotic organisms, the cell is capable of synthesizing many proteins. At any given time, many proteins which the cell is capable of synthesizing are not being synthesized. When a particular polypeptide, coded for by a given gene, is being synthesized by the cell, that gene is said to be expressed. In order to be expressed, the DNA sequence coding for that particular polypeptide must be properly located with respect to the control region of the gene. The function of the control region is to permit the expression of the gene under its control to be responsive to the changing needs of the cell at any given moment.

As used throughout this specification, the following definitions apply for purposes of the present invention:

A cloning vehicle is an extra-chromosomal length of duplex DNA comprising an intact replicon that can be replicated within a unicellular organism by transformation. Generally, cloning vehicles are derived from viruses and bacteria, and most commonly take the form of circular loops of bacterial DNA called plasmids.

The term gene refers to those DNA sequences which are responsible for the transmission and synthesis of a single protein chain.

The term infection refers to the invasion by pathogenic agents of cells where conditions are favorable for their replication and growth.

The term transfection refers to a technique for infecting cells with purified nucleic acids of viruses by precipitation of viral DNAs and uptake into cells upon addition of calcium chloride to solutions of DNA containing phosphate or other appropriate agents such as dextran sulfate.

A number of host-vector systems utilizing the above-described general scheme and techniques have been developed for use in the commercial or experimental synthesis of proteins by genetically modified organisms. Many of these host-vector systems are prokaryotic host-vector systems, such as that described in U.S. Pat. No. 4,338,397 to Gilbert, et al., and the system utilized for β-interferon synthesis in *Escherichia coli* as described by T. Taniguchi, et al., *Proc. Natl. Acad. Sci. U.S.A.* 77, 5230 (1980) (see also D. V. Goeddel, et al., *Nucleic Acid Res.* 8, 4057 (1980) and Y. Mory, et al., *Eur. J. Bio. Chem.* 120, 197 (1981). Additionally, systems have been utilized which employ yeast as a vector such as the system employed for hepatitis B surface antigen synthesis as described by A. Miyanohara, et al., *Proc. Natl. Acad. Sci. U.S.A.* 80, 1 (1983), and the system for human interferon synthesis within yeast described by Pitzeman, et al., *Science* 219, 620 (1983).

The value of utilizing yeast or prokaryotic host-vector systems for the synthesis of desirable proteins is diminished by certain limitations inherent in such systems. For instance, the mRNA transcript or protein product of such systems may be unstable in the prokaryote. In addition, before a protein will be synthesized within a prokaryotic cell, the DNA sequence introduced into the microorganism must be free of intervening DNA sequences, nonsense sequences, and initial or terminal sequences which encode for polypeptide sequences which do not comprise the active eukaryotic protein. Further, some eukaryotic proteins require modification after synthesis (i.e., glycosylation) to become biologically active, and prokaryotic cells are generally incapable of such modifications.

Additional limitations associated with yeast or prokaryotic host-vector systems include the relatively low level of gene expression and the difficulties associated with the recovery of gene products synthesized from within the cell. U.S. Pat. No. 4,336,336 to Silhavy, et al., is specifically addressed to the problem of recovering the gene products, providing a method for synthesis and secretion of the protein by a genetically modified bacterium.

The use of viruses in eukaryotic host-vector systems has been the subject of a considerable amount of recent investigation and speculation. However, viral vector systems also suffer from significant disadvantages and limitations which diminish their utility. For example, a number of eukaryotic viral vectors are either tumorgenic or oncogenic in mammalian systems, creating the potential for serious health and safety problems associated with resultant gene products and accidental infection. Further, in some eukaryotic host-viral vector systems, the gene product itself exhibits antiviral activity, thereby decreasing the yield of that protein. Such was the case with the 80% reduction in the yield of simian virus 40 caused by only 100 units of interferon in the eukaryotic host-viral vector system described by D. Gheysen and W. Fiers, *J. Molec. Applied Genet.* 1, 385–394 (1982).

Another problem inherent in those eukaryotic host-viral vector systems currently utilized is presented by the fact that, because they have fewer restriction sites, it is easier to insert exogenous DNA into simple viruses at specific locations. However, because of the morphology of the virus, the amount of exogenous DNA which can be packaged into a simple virus is limited. This limit becomes a particularly acute problem due to the fact that eukaryotic genes, because they usually contain intervening sequences, are too large to fit into simple viruses. Further, because they have many restriction sites, it is more difficult to insert exogenous DNA into complex viruses at specific locations.

The present invention overcomes many of the limitations discussed above by utilizing a baculovirus and a promoter within the baculovirus genome to produce a viral expression vector in a eukaryotic host-vector system. More particularly, the baculovirus *Autographa californica* (AcMNPV) and the polyhedrin promoter may be utilized to produce a recombinant viral expression vector capable of extremely high levels of expression of a selected gene in a eukaryotic host insect cell. Additionally, the resultant gene products of this system may be efficiently secreted into the cell medium, alleviating those difficulties associated with the recovery of protein products. Further, and more significantly, this system is not oncogenic or tumorgenic in mammals. The theoretical advantages of utilizing baculoviruses in a eukaryotic host-viral vector system are discussed in more detail by L. K. Miller, "A Virus Vector for Genetic Engineering in Invertebrates." *In*: Panopoulos, N. J. (Ed.), *Genetic Engineering in the Plant Sciences* (New York, Praeger Publishers, 1981), pp. 203-224.

SUMMARY OF THE INVENTION

In its broadest scope, the present invention provides a method for producing a recombinant viral expression vector capable of expression of a selected gene in a host insect cell.

In accordance with the present invention, baculovirus DNA comprising a baculovirus gene or a portion thereof which includes a promoter of said baculovirus gene is cleaved to obtain a DNA fragment containing at least said promoter. In the preferred method, DNA comprising the polyhedrin gene and flanking DNA sequences of an appropriate baculovirus, such as the preferred baculovirus *Autographa californica* (AcMNPV), is first isolated. The desired DNA is then cleaved by appropriate restriction procedures to produce a DNA fragment comprising the polyhedrin promoter and at least one DNA sequence encoding for the polyhedrin protein or a portion thereof. The preferred DNA fragment is an EcoRI-I fragment comprising the polyhedrin promoter and DNA sequences coding for the polyhedrin protein.

A recombinant shuttle vector is prepared by first inserting the DNA fragment described above into a suitable cloning vehicle, such as the preferred plasmid pUC8, so as to produce a shuttle vector. Accordingly, the preferred shuttle vector, designated as a polyhedrin shuttle vector, comprises the polyhedrin promoter and an available site for cloning a selected gene or portion thereof such that the selected gene is under the transcriptional control of the polyhedrin promoter. The preferred shuttle vector may or may not also contain DNA sequences coding for the polyhedrin protein or a portion thereof.

The recombinant shuttle vector is thereafter prepared by inserting a selected gene or portion thereof into the available cloning site of the above-described shuttle vector. While the preferred gene is the human IFN-β gene encoding for human β-interferon synthesis, it is recognized by those skilled in the art that potentially any gene or genes may be cloned into the shuttle vector of this invention and coupled with a baculovirus promoter sequence. Additionally, by appropriate recombinant DNA techniques, the DNA sequences encoding for polyhedrin protein may be deleted from the above-described preferred shuttle vector such that the resultant cloned gene product will be the selected protein. Alternatively, if no coding sequences for polyhedrin protein are deleted, or at least one coding sequence for polyhedrin protein is not deleted from the preferred shuttle vector, the resultant cloned gene product will be a hybrid or fused protein comprising the selected protein and the polyhedrin protein or a portion thereof.

The recombinant shuttle vector is then contacted with an appropriate baculovirus DNA so as to effect recombination, thereby producing a mixture of nonrecombinants and recombinants which have incorporated the desired genetic material into the baculovirus genome. The preferred means of accomplishing recombination is by the well known process of transfection.

Recombinant baculovirus expression vectors, capable of expression of the selected gene in host insect cells, are thereafter selected by the appropriate screening or genetic selection techniques from this mixture of recombinant and nonrecombinant baculoviruses. The preferred means of selection of the preferred expression vector is by identification and isolation of those viruses in the nuclei of the insect cells which are defective in the production of viral occlusions due to the insertional inactivation of the polyhedrin gene.

The present invention is also directed to the recombinant baculovirus expression vector produced by the method as described above. Such an expression vector comprises an infectious baculovirus containing at least one selected gene or portion thereof that is linked to the virus genome and is stable within it. During replication of the expression vector in insect cells or insects, the selected gene can be expressed either under the control of the baculovirus transcriptional signals or under the control of its own promoter. The preferred baculovirus expression vector is the recombinant AcMNPV virus containing the gene for β-interferon, inserted into the AcMNPV genome in a location such that it is under the transcriptional control of the polyhedrin promoter.

This invention is further directed to the polyhedrin shuttle vector described above and methods for producing same. The preferred polyhedrin shuttle vector, comprising at least the polyhedrin promoter sequence and an available cloning site for insertion of a selected gene or portion thereof such that the selected gene is under the transcriptional control of the polyhedrin promoter, may be utilized as an intermediate vehicle for the genetic manipulation of baculoviruses. The polyhedrin shuttle vector may contain all or a portion of the DNA sequences coding for the polyhedrin protein.

This invention is further directed to the recombinant shuttle vector described above and methods for producing same. The preferred recombinant shuttle vector of this invention, comprising a selected gene or portion thereof coupled with the polyhedrin promoter, may be utilized as a vehicle for incorporation of the desired genetic information into the baculovirus genome.

The present invention is predicated upon the use of a baculovirus promoter in a host-vector system to promote the expression of a selected gene in a eukaryotic host insect cell. In particular, because the polyhedrin protein is one of the most abundantly synthesized proteins within a viral-infected eukaryotic host cell, the preferred method involves the incorporation of a selected gene into an appropriate baculovirus such that it is coupled with the polyhedrin promoter. Such a recombinant baculovirus provides an effective mechanism for synthesis of a selected gene product. Accordingly, the present invention is of significant utility as extremely high levels of desired gene products, such as β-interferon, may be synthesized and efficiently secreted from host insect cells.

BRIEF DESCRIPTION OF THE DRAWINGS

FIG. 2 depicts the scheme for the construction of the preferred modified shuttle vectors pAc311, pAc360, pAc373 and pAc380 starting with the plasmids pI10, pUC8 and a synthetic BamHI linker, wherein the term "Library" represents a library of modified pB'Bal plasmids which may be constructed by inducing deletion mutations at each possible position in the polyhedrin gene. The plasmids pB'Bal 11, pB'Bal 60, pB'Bal 73 and pB'Bal 80 were then selected from this library of mutant plasmids for further modification into the shuttle vectors pAc311, pAc360, pAc373 and pAc380.

FIG. 3 schematically shows the nucleotide sequence of the polyhedrin gene of AcMNPV and the sequence immediately upstream of that gene. In addition to the location of the unique BamHI cloning site, the points at which the deletion mutations were induced to construct the preferred shuttle vectors pAc101, pAc311, pAc360, pAc373 and pAc380 are indicated by the arrows. The "TATA" and "CAAT" boxes of the polyhedrin gene are indicated by rectangles drawn around those sequences and the transcriptional start site of the gene is indicated by the asterisks. FIG. 3 also shows the EcoRV and the HindIII restriction sites located within the polyhedrin gene.

FIG. 4 also shows the starting material plasmid pBR13, which contains the IFN-β gene, the plasmid pUC8 and a synthetic octanucleotide BamHI linker.

FIG. 5 depicts the scheme for the transfection of the preferred recombinant expression vector pAc380-IFN-β with wild type baculoviruses in cultured *Spodoptera frugiperda* cells and the subsequent infection of cultured *S. frugiperda* cells with the plaque-purified recombinant baculoviruses

DETAILED DESCRIPTION OF THE INVENTION

Figure 1:
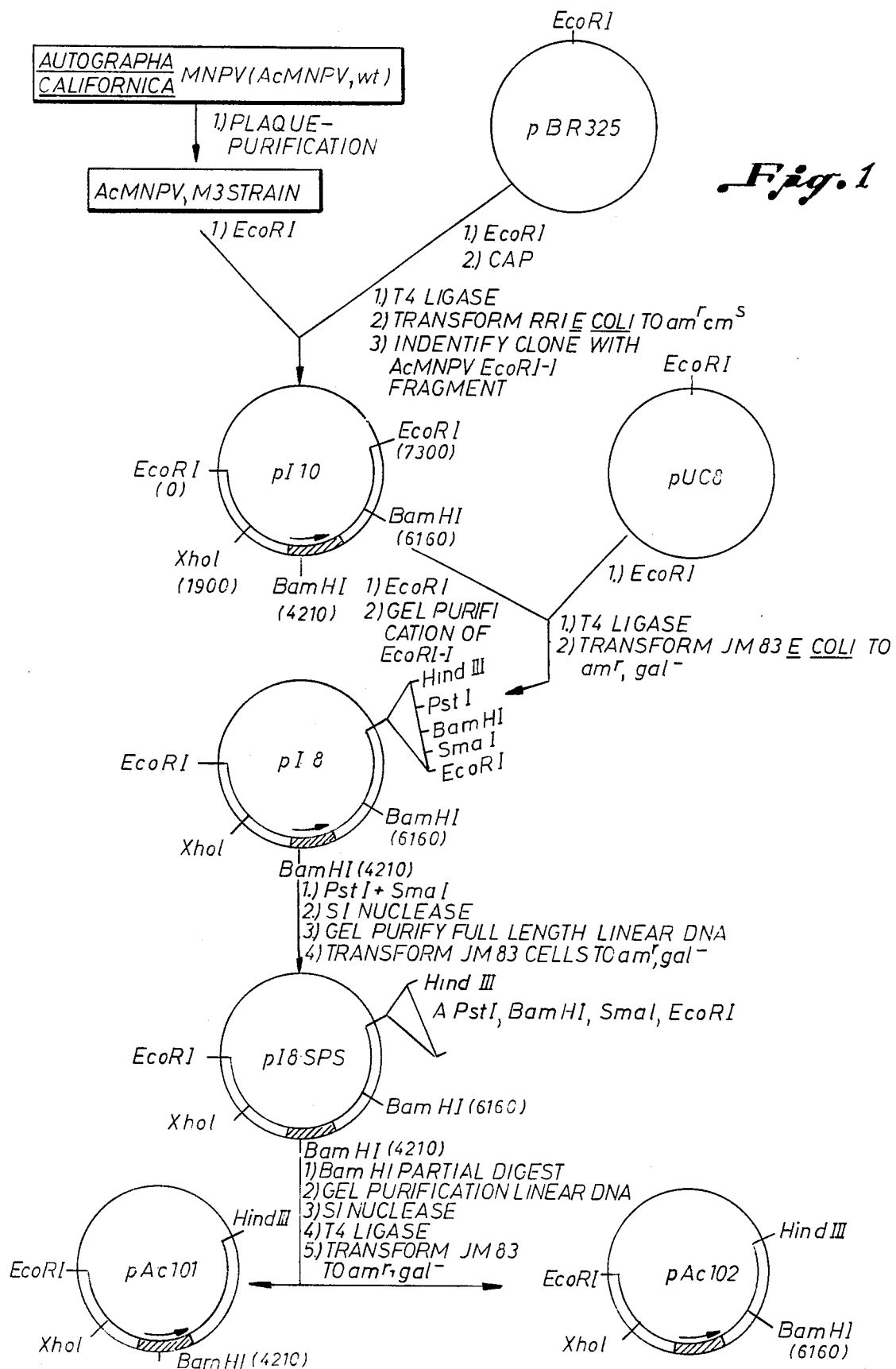
FIG. 1 depicts the scheme for the construction of one of the preferred shuttle vectors, pAc101, starting with a plaque-purified strain of AcMNPV, M3, the plasmid pBR325, and the plasmid pUC8.

The preferred baculovirus which may be utilized in the practice of the present invention is *Autographa californica* (AcMNPV). This baculovirus may be characterized as follows.

In its naturally occurring, infectious form, AcMNPV is usually found in a viral occlusion. These viral occlusions usually contain several virus particles embedded in a paracrystalline protein matrix comprising a structured array of polyhedrin protein subunits. An occlusion is ingested by an appropriate host insect, and when it reaches the lumen of the gut, the alkaline conditions cause the disassociation of the occlusion to release the virus.

The viruses invade the cells of the wall of the gut, migrate to the nucleus of those cells and replicate. Two infectious forms are produced in these cells, the extracellular, or nonoccluded virus form and the occluded virus. The extracellular virus buds from the surface of the cell to infect other cells. At approximately twelve hours after infection, there is a decrease in extracellular virus budding and the initiation of the synthesis of polyhedrin and an increased number of occluded virus particles are produced. Very large numbers of occlusions are produced in infected cells and tissues, ultimately lysing the insect. This occluded form of the virus is responsible for the spreading of infection to other insects.

It is the extracellular virus which can be easily cultured in cell culture medium and which is used in the preferred method of the present invention. The extracellular and occluded virus have the same genome, but exhibit different phenotypic properties.

The major component of these occlusions, polyhedrin, is a protein of approximately 33,000 molecular weight. Characterization of the AcMNPV genome in this laboratory indicates that the gene for AcMNPV polyhedrin maps to a contiguous DNA sequence of about 1200 base pairs in the EcoRI-I fragment at about 4000 base pairs down stream from the zero point of the DNA restriction map (see G. E. Smith, J. M. Vlak and M. D. Summers, *J. Virol*, 45, 215–225 (1983), which is hereby incorporated by reference). A map of the entire AcMNPV genome may be found in J. M. Vlak and G. E. Smith, *J. Virol.* 41, 1118–1121 (1982), hereby incorporated by reference.

The structure and function of the polyhedrin protein are of considerable interest because it is one of the most highly expressed eukaryotic genes known. In *Spodoptera frugiperda* cells infected with AcMNPV, polyhedrin accumulates to such high levels that it forms 25% or more of the total mass of the protein in a cell. The gene is also of interest for the following reasons: (1) the polyhedrin gene of AcMNPV contains DNA sequences that are highly conserved among baculoviruses, (2) recombination between closely related strains occurs at a high frequency in this region of the genome, thus allowing the segregation and expression of the polyhedrin gene in recombinant progeny, (3) expression of the gene is host, tissue, and cell line dependent, and (4) it may be that the control mechanisms associated with the synthesis of polyhedrin can be related to the incorporation of AcMNPV particles into occlusions.

From the point of view of a genetic engineer, the genes controlling the expression of the polyhedrin protein are unnecessary because the virus is capable of replication in cell culture even without them. Because of the high degree of expression of this gene and the fact that it is not essential to the continued ability of the virus to replicate, the possibility of using the polyhedrin promoter and gene of AcMNPV as part of a system for the expression of a recombinant gene has been the source of consideration speculation (see E. B. Carstens, S. T. Tjia and W. Doerfler, *Virology* 99, 386–398 (1979); P. Dobos and M. A. Cochran, *Virology* 103, 446–464 (1980); H. A. Wood, *Virology* 102, 21–27 (1980); J. E. Maruniak and M. D. Summers, *Virology* 109, 25–34 (1981); L. K. Miller, "A Virus Vector for Genetic Engineering in Invertebrates," *In*: N. J. Panopoulos (Ed.), *Genetic Engineering in the Plant Sciences* (New York, Praeger Publishers, 1981), pp. 203–224; and L. K. Miller, et al., *Science* 219, 715–721 (1983)). However, prior to the present invention, no one has been able to develop such a system.

Experimentation in this laboratory indicates that another gene product, 10K, is also expressed at a high level comparable to polyhedrin (G. E. Smith, J. M. Vlak and M. D. Summers, *J. Virol.* 45, 215–225 (1983), hereby incorporated by reference), and secreted into the culture medium from infected cells. Most of the 10K protein produced is apparently nonstructural, but the fact that it is produced late in infection and in large quantity suggests that it may be involved in the occlusion process. The location of the 10K AcMNPV protein gene maps between the HindIII fragments P and Q. Like the polyhedrin promoter and structural gene, this promoter has been the object of speculation as to its advantageous use as part of a system using AcMNPV for the expression of a recombinant gene. However, until the present invention, a system which would allow such advantageous use of this promoter had not been developed.

According to the preferred method of this invention, a particular strain of AcMNPV, M3, may be utilized. However, those skilled in the art who have the benefit of this disclosure will recognize that other baculoviruses and other baculovirus strains may also be suitably utilized to produce a recombinant baculovirus expression vector. In particular, it is expected that at least the closely related and naturally occurring strains *Trichoplusia ni* MNPV, *Rachiplusia ou* MNPV, *Galleria mellonella* MNPV and any plaque-purified strains such as the E2, R9, S1 and S3 strains of AcMNPV characterized in this laboratory and described in G. E. Smith and M. D. Summers, *J. Virol.* 30, 828–838 (1979) and G. E. Smith and M. D. Summers, *J. Virol.* 33, 311–319 (1980) (hereby incorporated by reference) may be utilized to advantage. Further descriptions of these and other strains are found in G. E. Smith and M. D. Summers, *Virology* 89, 517–527 (1978), also incorporated by reference.

In accordance with the method of this invention, it is the polyhedrin structural gene and promoter which are utilized to advantage. This gene has been mapped by S1 nuclease experiments in this laboratory; the nucleotide sequence of the 5' end of the polyhedrin coding region and 200 bases upstream from the start of transcription are shown in FIG. 3. Although experiments in this laboratory indicate that other transcriptional start sites may exist (see G. E. Smith, J. M. Vlak and M. D. Summers, *J. Virol.* 45, 215–225 (1983)), the site indicated in FIG. 3 is the most frequently used transcriptional start site for polyhedrin mRNA.

An ATG translation start signal (with the A residue assigned position +1) occurs approximately 45 bases from the transcriptional start site, followed by an open reading up to and including the HindIII site at 255. The "TATA" and "CAAT" boxes found in similar positions in many eukaryotic structural genes are located between 25 and 35 bases and between 60 and 70 bases upstream from the transcriptional start site respectively. Centered at 78 and 90 bases upstream from the transcriptional start site are the direct repeated sequences "CACAAACT". In addition, the AcMNPV polyhedrin gene has a 45 base nontranslated leader sequence preceding the translational start codon and, as suggested by appropriate experimental procedures on AcMNPV polyhedrin mRNA, there are no intervening sequences. See, Smith, Vlak and Summers, supra and G. F. Rohrman, et al., *Virology* 121, 51–60 (1982).

To practice the preferred method of the present invention, DNA having a polyhedrin gene is isolated and purified from the baculovirus AcMNPV. It will be recognized by those skilled in the art who have the benefit of this disclosure that this gene could be isolated from any baculovirus which possesses a polyhedrin gene, particularly the related strains described above.

The desired DNA is then digested with EcoRI restriction endonuclease by appropriate restriction procedures to produce a 7.3 kilobase EcoRI-I fragment comprising the polyhedrin gene.

The EcoRI-I fragment described above is thereafter cloned into the EcoRI site of an appropriate cloning vehicle to produce a shuttle vector. Because the AcMNPV genome has no known unique restriction sites into which selected genes may be effectively introduced in a site-specific manner, it is necessary to construct chimeric plasmid vectors (shuttle vectors) to serve as intermediate vehicles for gene transfer. Therefore, to incorporate selected genes into the viral genome adjacent to the polyhedrin promoter sequence, a shuttle vector is constructed, designated as the polyhedrin shuttle vector, which comprises the polyhedrin gene, a cloning site located such that a gene properly inserted into the site will be under the control of the polyhedrin promoter, and flanking viral DNA linked to either side of the polyhedrin gene. The construction of this shuttle vector using the preferred materials is schematically shown in FIG. 1. Additionally, it should be noted that the presence of flanking viral DNA facilitates recombination with the wild type baculovirus, allowing the transfer of a selected gene into a replicating viral genome.

Accordingly, the EcoRI-I fragment described above is cloned and subcloned into the preferred plasmids pBR325 and pUC8, respectively. Two BamHI restriction sites in the EcoRI-I fragment may thereafter be removed so as to produce a preferred polyhedrin shuttle vector, designated as pAc101, having a single BamHI cloning site located in the 3' direction downstream from the polyhedrin promoter sequence approximately 220 bases from the translational start site of the polyhedrin gene (See FIG. 3). While plasmids pBR325 and pUC8 are the preferred plasmids utilized for construction of the polyhedrin shuttle vector, it will be recognized by those skilled in the art that other suitable cloning vehicles may be utilized provided that the polyhedrin gene and flanking viral DNA may be functionally incorporated.

The polyhedrin shuttle vector may thereafter be modified for insertion of a selected gene by deleting some or all of the sequences encoding for polyhedrin synthesis near the transcriptional start site or from about −45 to the end of the polyhedrin gene (See FIG. 3). A DNA linker, comprising a natural or synthetic oligonucleotide bearing the BamHI restriction site sequence, is then inserted at the site of the deletion to allow the coupling of DNA segments at that restriction site. The preferred modification of the shuttle vectors using the preferred materials is shown schematically in FIG. 2 and the preferred means of deleting polyhedrin coding sequences is by in vitro mutagenesis. However, it will be recognized by those skilled in the art who have the benefit of this disclosure that alternative procedures are available to delete polyhedrin coding sequences, that alternative synthetic or natural oligonucleotide linker sequences could be inserted at the site of the deletion, and that alternative modified polyhedrin shuttle vectors into which a selected gene or portion thereof may be incorporated may be suitably utilized in the present invention.

Figure 4:
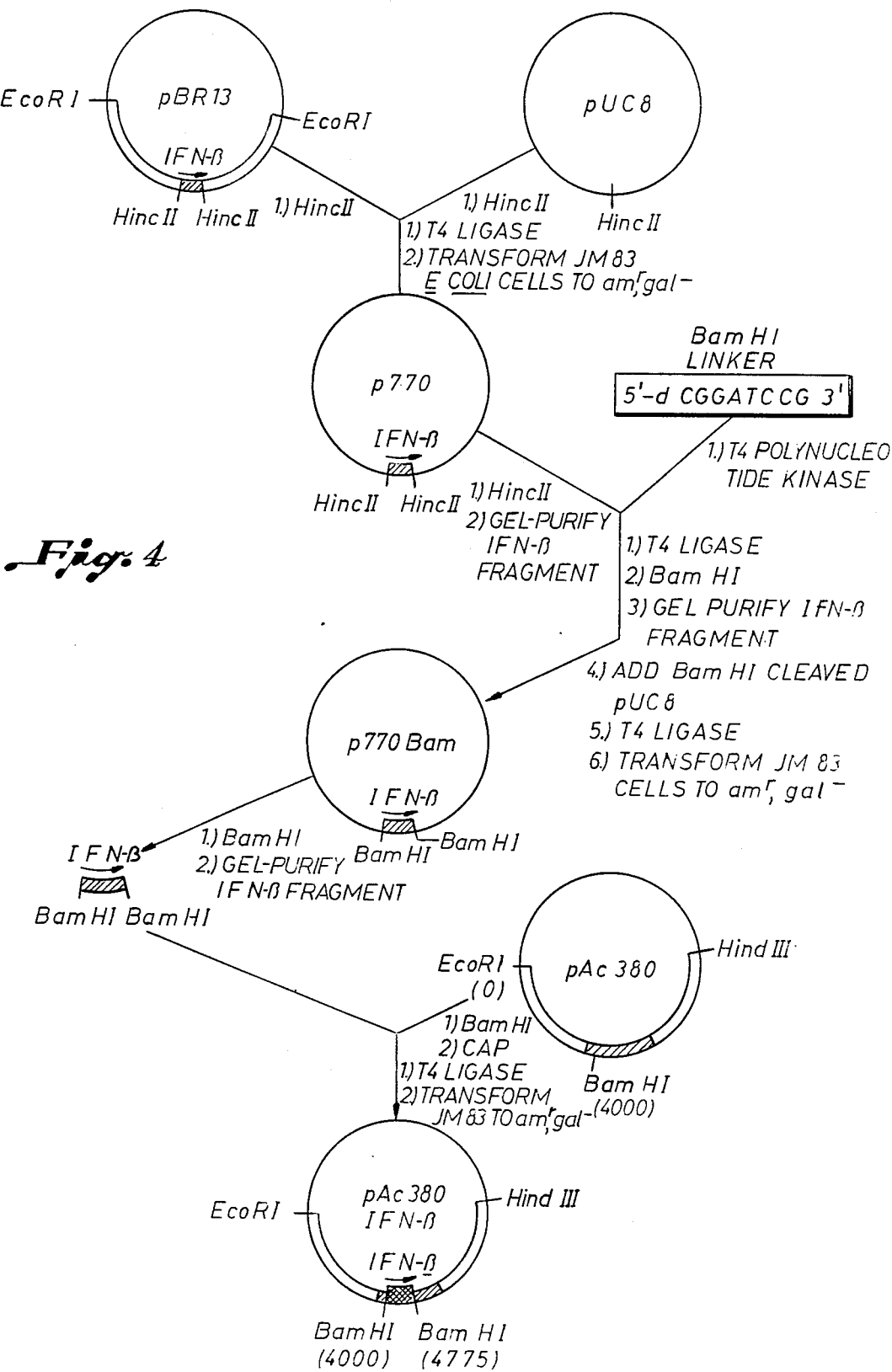
FIG. 4 depicts the scheme for the cloning of the preferred IFN-β gene into the preferred shuttle vector pAc380 to construct the recombinant expression vector pAc380-IFN-β.
Figure 6:
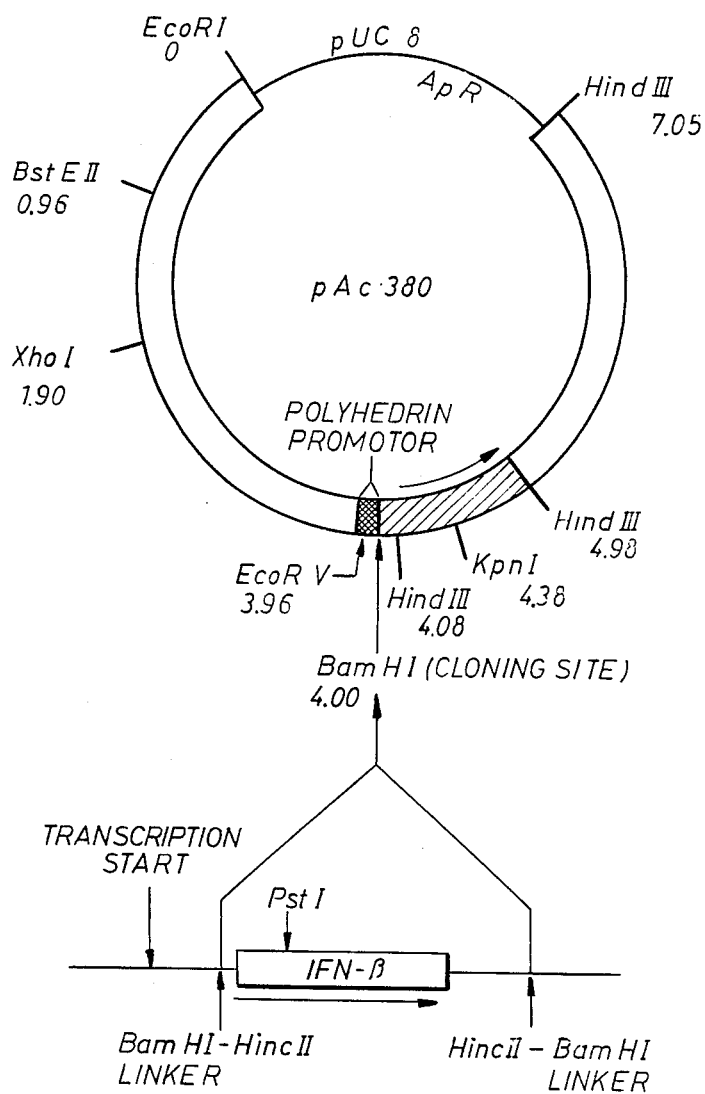
FIG. 6 shows the preferred recombinant shuttle vector pAc380-IFN-β with the IFN-β gene inserted at the BamHI cloning site of the EcoRI fragment of the AcMNPV genome. The polyhedrin promoter sequence is indicated in solid black and the EcoRI-I sequence is shown as being incorporated into the preferred plasmid pUC8.

In accordance with standard cloning techniques, a selected gene, such as the preferred IFN-β gene encoding for human β-interferon synthesis, is thereafter inserted into the polyhedrin shuttle vector at the available restriction site to produce a recombinant shuttle vector. Insertion of this gene using the preferred materials is shown schematically in FIG. 4. The insertion of the IFN-β gene will produce a hybrid or fused polyhedrin-IFN-β gene capable of producing a fused polypeptide product if only a portion of the polyhedrin gene was deleted as described above or, if the entire structural sequence was deleted, only interferon will be produced. Further, the hybrid gene comprises the polyhedrin promoter, the IFN-β protein coding sequences, and sequences encoding for a portion of the polypeptide sequence of the polyhedrin protein, provided all such coding sequences are not deleted from the particular polyhedrin shuttle vector utilized.

It will be recognized by those skilled in the art who have the benefit of this disclosure that the above-described linker sequence bearing an appropriate restriction site need not be inserted in place of all or a portion of the polyhedrin structural sequence, and that it would be possible to insert the linker in locations in the baculovirus genome such that both the sequence coding for the selected polypeptide and the polyhedrin structural sequence would be expressed. For instance, the sequence coding for the selected polypeptide could be inserted into the 10K gene in place of all or a portion of the 10K structural sequence and under the transcriptional control of the 10K promoter. Further, while the IFN-β gene is the preferred gene for cloning into the polyhedrin shuttle vector and coupling with the polyhedrin promoter sequence, it will be recognized that potentially any gene may be utilized in the present invention or in its above described alternative forms.

Figure 5:
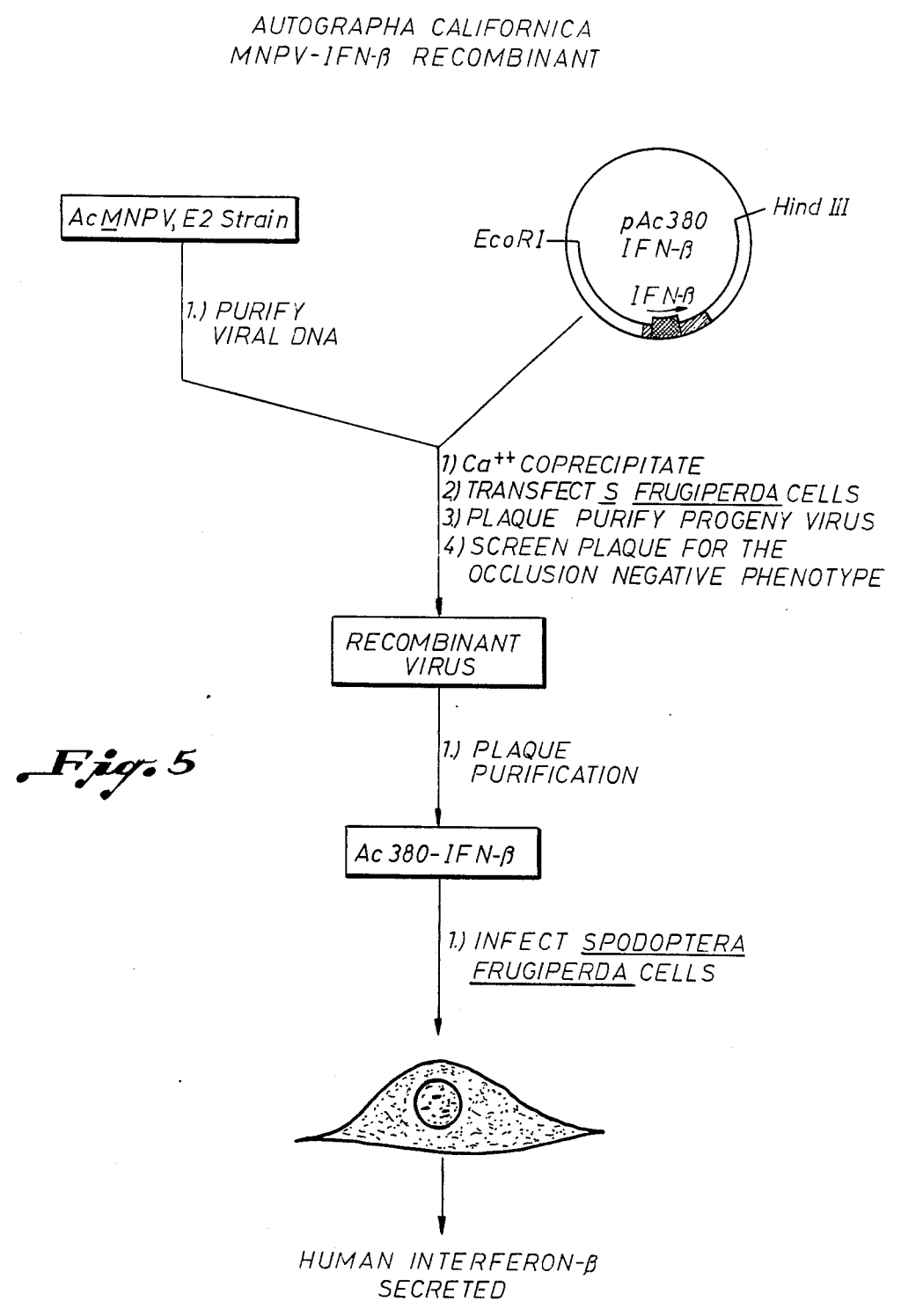

The hybrid polyhedrin-IFN-β gene of the recombinant shuttle vector is thereafter transferred into the genome of an appropriate baculovirus, such as the preferred baculovirus AcMNPV to produce a recombinant viral expression vector capable of expressing the gene encoding for β-interferon in a host insect cell. Transfer of the hybrid gene is accomplished by the process of transfection in host insect cells, such as *Spodoptera frugiperda*. J. P. Burand, et al., *Virology* 101, 286–290 (1980). This process is shown schematically in FIG. 5, utilizing the preferred recombinant shuttle vector pAc380-IFN-β. During replication of the AcMNPV DNA after transfection, the hybrid gene is transferred to AcMNPV DNA by recombination between the recombinant shuttle vector and AcMNPV DNA. Accordingly, a mixture is produced comprising nonrecombinant and recombinant baculoviruses capable of expressing the IFN-β gene. While transfection is the preferred process for transfer of the hybrid gene into the baculovirus genome, it will be understood by those skilled in the art that other procedures may be suitably utilized so as to effect the insertion of the gene into the baculovirus genome and that recombination may be accomplished between the recombinant shuttle vector and other strains of baculoviruses, as long as there is sufficient homology between the sequence of the hybrid gene and the corresponding sequence of the other strain to allow recombination to occur. For instance, it is expected that such recombination could occur between genes isolated from any of the above-described strains *Trichoplusia ni* MNPV, *Rachiplusia ou* MNPV, and *Galleria mellonella* MNPV, as well as the AcMNPV strains E2, R9, S1 and S3.

The preferred recombinant AcMNPV expression vector, comprising the hybrid polyhedrin IFN-β gene incorporated into the AcMNPV genome, is thereafter selected from the mixture of nonrecombinant and recombinant baculoviruses. The preferred means of selection is by screening for plaques formed by host insect cells infected with viruses that do not produce viral occlusions (designated as 0−). Selection may be performed in this manner because recombinant viruses are defective in the production of viral occlusions due to the insertional inactivation of the polyhedrin gene. Of the viral plaques produced from the progeny virus from transfected cells, an average of 0.5% will be from putative recombinant 0− viruses. Accordingly, the DNA from an 0− plaque-forming recombinant virus is thereafter purified and may be analyzed with appropriate restriction enzymes to confirm that the recombinant AcMNPV vector has an insertion of the selected gene in the proper EcoRI-I location. The above-described selection procedure provides an effective and convenient means for selection of recombinant baculovirus IFN-β expression vectors, however it will be recognized by those skilled in the art that alternative selection procedures may also be utilized in accordance with the present invention.

Expression of the selected gene is accomplished by infecting susceptible host insect cells, such as the preferred *Spodoptera frugiperda*, with the recombinant baculovirus IFN- expression vector in an appropriate medium for growth. An AcMNPV expression vector is propagated in insect cells or insects through replication and assembly of infectious virus particles. These infectious AcMNPV expression vectors can be used to produce the selected gene in suitable insect cells, thus facilitating the efficient expression of the selected DNA sequence in the infected cell.

During infection, AcMNPV expression vector-specific mRNA will be produced that is complementary to the DNA sequence of the selected gene. The vector-specific mRNA will usually be translated in infected cells to produce a protein that is completely or partially coded for by the selected gene and in some instances, the selected gene product will undergo processing such as glycosylation or secretion. Because the cloned gene contains the DNA sequences for a signal peptide (see Hitzeman, et al., *Science* 219, 620–626 (1983) and references therein),β-interferon may then be purified from the culture medium. Although not as advantageous, the cloned gene may be utilized without such sequences, in which case the gene product must be extracted from the insect cells.

Whether the gene product produced by the preferred recombinant AcMNPV expression vector consists of the amino acid sequences of only the selected protein, is a hybrid protein containing one or more additional amino acid residues derived from the amino terminal end of AcMNPV polyhedrin, or whether both selected and hybrid protein products are produced is dependent upon the manner in which the polyhedrin shuttle vectors are modified. If only a single translational start signal (ATG) derived from the selected gene is present in the hybrid gene sequences, and the selected gene is present in the hybrid gene sequences between about the −75 and +1 positions, then only the selected protein, β-interferon, will be produced (see FIG. 3). Alternatively, if the selected gene is fused to the polyhedrin promotor such that there are two translational start sites, the polyhedrin ATG signal at +1 and the selected gene ATG signal at between +3 and +175, both the hybrid and selected proteins are likely to be produced. However, the proportion of each protein produced may vary depending on the position of the second ATG signal and the nature of the selected gene sequences. Alternatively, if a gene is fused to the polyhedrin promotor without its own ATG start signal, then it will require that either a synthetic ATG or the polyhedrin ATG translation start signal be fused to the protein coding sequences in such a way as to maintain the correct translational reading frame for the selected gene. The protein products that will be produced will, again, depend upon the factors described above.

DEPOSIT OF RECOMBINANT EXPRESSION VECTOR AND PLASMID

The preferred recombinant baculovirus expression vector Ac380-IFN-β was deposited with the American Type Culture Collection (Rockville, Md.) on May 13, 1983, and assigned accession number ATCC 40071. The preferred modified polyhedrin shuttle vector pAc380 plasmid in E. coli K-12 and the preferred recombinant shuttle vector pAc380-IFN-β in E. coli K-12 were both deposited with the Agricultural Research Culture Collection (Peoria, Ill.) on May 13, 1983, and assigned the accession numbers NRRL B-15428 and NRRL B-15427, respectively.

STARTING MATERIALS AND METHODS

Plasmid DNA

The plasmids used in the following examples were pBR325 and pUC8 in E. coli, and were obtained from Bethesda Research Labs, Gaithersburg, Md.

Viral DNA

AcMNPV, strain M3, used in the examples as the original source of viral DNA, as well as AcMNPV, strain E2 and wild type, were isolated in this laboratory (see G. E. Smith and M. D. Summers, Virology 89, 517–520 (1978) and G. E. Smith and M.D. Summers, J. Virol 39, 125–137 (1981)).

IFN-β DNA

The DNA fragment comprising the IFN-β gene used in the examples was isolated from the plasmid pBR13, obtained from Dr. John Collins, Gesellschaft fur Biotechnologische Forschung (GBF), Braunschweig Stockhein, West Germany.

Bacterial Cells

E. coli JM83, used in the examples for cloning pUC8 plasmids, was obtained from Bethesda Research Labs, Gaithersburg, Md.

E coli RR1, used in the examples for cloning pBR325 plasmids, was obtained from Dr. Savio Woo, Baylor College of Medicine, Houston, Tex.

Enzymes

The following restriction endonucleases were obtained from Bethesda Research Laboratories, Gaithersburg, Md., and used according to that supplier's recommendations: EcoRI, XhoI, BamHI, SmaI, PstI and HindIII. The following enzymes were also obtained from Bethesda Research Laboratories: calf intestinal alkaline phosphatase (CAP), T4 DNA ligase, Bal31 exonuclease, S1 nuclease and T4 polynucleotide kinase.

Methods

The standard methods used in accordance with the cloning procedures set forth in the examples are described in T. Maniatis, E. F. Fritsch and J. Sambrook, *Molecular Cloning: A Laboratory Manual*, Cold Spring Harbor Laboratory, 1982, which is herein incorporated by reference. This reference includes procedures for the following standard methods: cloning procedures with E. coli plasmids, transformation of E. coli cells, plasmid DNA purification, phenol extraction of DNA, ethanol precipitation of DNA, agarose gel electrophoresis, purification of DNA fragments from agarose gels, and restriction endonuclease and other DNA-modifying enzyme reactions. In all cases, DNA was purified by phenol extraction followed by ethanol precipitation.

Virus stocks used in the examples were prepared and titrated in *Spodoptera frugiperda* cells (IPLB-Sf 21-AE) with TNM-FH medium (see W. F. Hink, *Nature (London)* 226, 466–467 (1970), which is herein incorporated by reference) plus 10% fetal bovine serum. The procedures for the cultivation of viruses and cells are described in L. E. Volkman and M. D. Summers, *J. Virol.* 19, 820–832 (1975) and L. E. Volkman, M. D. Summers and C. H. Hsieh, *J. Virol.* 19, 820–832 (1976), which are herein incorporated by reference. Viral growth kinetics were determined as described by Volkman, et al., supra, using *S. frugiperda* and a 1.5% agarose overlay.

EXAMPLE I

Construction of Polyhedrin Shuttle Vector

To construct a polyhedrin shuttle vector according to the present invention, a DNA fragment comprising the AcMNPV polyhedrin gene was cloned into the EcoRI site of the plasmid pUC8. This was accomplished by using a plaque-purified strain of AcMNPV, designated M3 (G. E. Smith and M. D. Summers, *Virology* 89, 517–527 (1978), herein incorporated by reference) as the original source of the viral DNA. AcMNPV DNA was extracted from the virus and purified by equilibrium centrifugation in cesium chloride density gradients as described in the above-referenced reference by Smith and Summers. AcMNPV DNA was digested to completion with EcoRI restriction endonuclease. The resulting AcMNPV EcoRI-I fragment was first cloned into pBR325 to form pI10, then subcloned into pUC8 using standard cloning procedures to form pI8 (see FIG. 1A).

The recombinant plasmid pI8 has three BamHI recognition sites (see FIG. 1C): one in the polyhedrin gene at position 4210, one in pUC8 at 7300 and one in the EcoRI-I fragment at position 6160. The sites at 6160 and 7300 must be removed from pI8 so that the desired gene, in this case, the preferred IFN-β gene, may conveniently be cloned into pI8 in the desired location (position 4210) adjacent to the polyhedrin promoter.

The pUC8 BamHI restriction site in pI8 at about 7300, which is not located in the polyhedrin gene, was removed as follows: 10 μg of pI8 was digested with PstI and SmaI, the DNA purified, and resuspended in S1 nuclease buffer (0.03M sodium acetate, pH 4.4, 0.25M NaCl and 0.0045M ZnCl₂) plus 500 units S1 nuclease/ml. The reaction mix was incubated at 37° C. for 15 minutes, then the DNA electrophoresed in an 0.8% agarose gel. High molecular weight linear DNA was purified from the gel and used to transform *E. coli* JM83 cells to ampicillin resistant (am$^r$), galactosidase negative (gal$^-$). A plasmid was isolated that was missing the PstI, BamHI, SmaI, and EcoRI sites in the pUC8 cloning region. This plasmid was designated pI8SPS (see FIG. 1B).

The BamHI site at location 6160 (Smith, G. E., J. M. Vlak and M. D. Summers, *J. Virol.* 45: 215-225) in AcMNPV EcoRI-I (a part of pI8SPS) was removed as follows: 10 μg of pI8SPS was mixed with 10 units of BamHI in 50 μl of buffer and incubated at 37° C. 10 μl aliquots were removed after 3, 6, 12, 20, and 30 minutes and the reactions stopped by adding EDTA to 10 mM. The aliquots were pooled and electrophoresed in 0.7% agarose. Full length linear DNA was isolated from the gels, treated with S1 nuclease as above, then circularized with T4 DNA ligase. JM83 cells were transformed to am$^r$, gal$^-$ and a recombinant plasmid was identified that was missing the BamHI restriction site at position 6160. This plasmid has a single BamHI cloning site at position 4210 located +175 bases from the translation start site of the polyhedrin gene (see FIG. 3) and was designated pAc101, the "parent" AcMNPV polyhedrin gene shuttle vector (FIG. 1C).

EXAMPLE II

Modification of Shuttle Vector

In order to determine the best location in the polyhedrin gene for the insertion of the selected gene, a number of shuttle vectors were constructed in addition to pAc101(see FIG. 2). These shuttle vectors were constructed by deleting some or all of the DNA sequence that encodes the 86 amino-terminal residues of polyhedrin and the 5' non-translated polyhedrin mRNA sequences, and then inserting an oligonucleotide synthetic DNA linker with a BamHI recognition site at the site of the deletion by the following procedures.

In the same manner as set forth in Example I, the EcoRI to BamHI fragment (0 to 4210) from pI10 was subcloned into pUC8 and the resulting plasmid was designed pB' (see FIG. 2A). This fragment contains polyhedrin gene up to +175 and about 4000 base pairs of AcMNPV DNA sequences in addition to the polyhedrin gene. Deletions around the BamHI site at position 4210 were then introduced into pB' as follows (FIG. 2B): 40 μg of pB' was digested with BamHI, the DNA was purified, and electrophoresed on an 0.7% agarose gel. The linear DNA fragment was extracted from the gel and incubated in 100 μl of buffer with 0.5 units of Bal31 exonuclease for 40 minutes at 30° C. 10 μl aliquots were collected at 1, 2, 5, 10, 15, 20, 25, 30, 35 and 40 minute intervals and the reaction stopped by adding 10 μl 0.25M EDTA to each aliquot. The aliquots were pooled and the DNA purified. The ends of the DNA were repaired by incubating in 100 μl of buffer for 30 minutes at 23° C. with 4 units *E. coli* DNA polymerase (Klenow fragment). The DNA was purified and 1 μg of phosphorylated BamHI linker (5'-dCGGATCCpG-3') was added plus 20 units T4 DNA ligase in 100 μl reaction mix. After incubation for 2 hours at room temperature, the DNA was purified.

Next, the DNA pellet was resuspended in 100 μl of buffer plus 20 units BamHI and digested for 4 hours at 37° C. The digested DNA was electrophoresed in 0.7% agarose and pB' truncated plasmids with up to 800 base pair deletions were purified from the gel. The DNA was circularized with T4 DNA ligase and used to transform JM83 cells to am$^r$, gal$^-$. The resulting clones constituted the "LIBRARY" of mutant plasmids designated pB'Bal 1, 2, 3, and so on depending upon the location of the BamHI recognition site.

Several pB'Bal deletion mutant plasmids were selected and the XhoI (1900) to the BamHI linker (at positions 4000 to 4210) fragment from each was purified from an agarose gel (A fragments)(FIG. 2B). The XhoI (1900) to BamHI (4210) fragment was removed from pAc101and the remaining sequences purified from an agarose gel (B fragment)(FIG. 2C). About 0.1 μg of each of the A fragments were mixed with 0.1 μg of Fragment B, joined by incubating in 20 μl of buffer with 1 unit of T4 DNA ligase, then used to transform JM83 cells to am$^r$, gal$^-$. The resulting plasmids were the modified shuttle vectors and referred to as, for example, pAc311if derived from pB'Bal 11, pAc360 if derived from pB'Bal 60, and so on. In this manner, a group of "modified" shuttle vectors was constructed with representatives having BamHI cloning sites at all possible positions between +175 and -100 in the polyhedrin gene. The location of the BamHI recognition site in four of the modified shuttle vectors, pAc380, pAc373, pAc311and pAc360, as well as its location in the parent shuttle vector, pAc101, is shown in FIG. 3.

EXAMPLE III

Constructing Recombinant Shuttle Vector Comprising Polyhedrin - IFN-β Gene

Any one of the shuttle vectors prepared according to the methods of Examples I or II may be utilized in the construction of the preferred recombinant shuttle vector in which the desired gene is linked to the polyhedrin gene at various locations, depending upon the particular modified shuttle vector utilized. The insertion of the preferred IFN-β gene encoding for human β-interferon synthesis into one of the preferred modified shuttle vectors, pAc380, at the single BamHI cloning site using standard cloning techniques as referenced above to form the plasmid designated pAc380-IFN-β is shown schematically in FIG. 4.

The preferred IFN-β gene may be characterized as a 0.767 kilobase HincII fragment, obtained from a genomic clone of human IFN-β$_1$ (designated pBR13, see H. Hauser, et al., *Nature (London)* 297, 650-654 (1982) and G. Gross, et al., *Nucleic Acids Res.* 9, 2495-2507 (1981)), and containing the entire protein coding sequences for IFN-β, three additional bases before the ATG translation start signal, and all of the non-translated 3' sequences including the signal for polyadenylation. The nucleotide sequence for IFN-β and the location of various transcription and translation signals are described by R. Derynck, et al., *Nature (London)* 285, 542-547 (1980); G. Gross, et al., *Nucl. Acids. Res.* 9, 2495-2507 (1981); and S. Ohno and T. Taniguchi, *Proc. Natl. Acad. Sci. USA* 78, 3505-3509 (1981), which are herein incorporated by reference.

The HincII DNA fragment comprising the IFN-β gene is inserted into the available BamHI restriction site of pAc380 using synthetic oligonucleotide linkers on the IFN-β gene fragment such that insertion is adjacent to the AcMNPV polyhedrin promoter and in the same 5' to 3' orientation as the polyhedrin gene.

In essentially the same manner, the IFN-β gene was cloned into the other preferred modified shuttle vectors pAc311, pAc360 and pAc373 and the parent shuttle vector pAc101 to form the recombinant shuttle vectors designated pAc311-IFN-β, pAc360-IFN-β, pAc373-

IFN-β and pAc101-IFN-β, respectively. Potentially, that gene, or any other, could be cloned into any of the shuttle vectors with the BamHI recognition site inserted at any location in the shuttle vector. Further, it would not be necessary to delete the polyhedrin structural sequence to insert the BamHI recognition site, as deletions could be induced at any point in any fragment of the AcMNPV genome which could be incorporated into a plasmid as outlined in Example I.

EXAMPLE IV

Transfer of Polyhedrin - IFN-β Gene to AcMNPV Genome

Any of the preferred recombinant shuttle vectors prepared by the method of Example III may thereafter be utilized to transfer the preferred IFN-β gene into the genome of AcMNPV to form a recombinant baculovirus expression vector. The preferred method by which this transfer may be effected is by transfection in the presence of $Ca^{++}$ and susceptible insect host cells such as *S. frugiperda*.

A modification of the method described by F. L. Graham and A. J. Van Der Eb, *Virology* 52, 456–467 (1973), hereby incorporated by reference, was utilized as follows: DNA extracted and purified from AcMNPV (1 μg) was mixed with 1 to 10 μg of the recombinant shuttle vector DNA, in particular, the preferred recombinant shuttle vector pAc380-IFN-β and brought to 950 μl in 1-HEPES (N-2-hydroxyethyl-piperazine-N'-2-ethanesulfonic acid)-buffered saline (pH 7.05) with 15 μg of carrier calf thymus DNA per milliliter. While the mixture was being stirred in a Vortex mixer, 50 ml of 2.5M $CaCl_2$ was added dropwise, and a precipitate was allowed to form at room temperature for 30 minutes. One milliliter of precipitated DNA was added to susceptible insect host cells, in this case, *S. frugiperda*, in 2 ml of medium in 60 mm culture plates. After 4 hours, the cell monolayer was washed with medium and incubated in 2 ml of medium with 10% fetal bovine serum for 3 days. The resulting progeny constituted a mixture of recombinant and nonrecombinant AcMNPV viruses.

EXAMPLE V

Selection of Recombinant AcMNPV Expression Vector

It was next necessary to isolate an AcMNPV recombinant expression vector from the resultant mixture of nonrecombinant and recombinant baculoviruses described by Example IV. The preferred method by which this isolation was accomplished in those recombinants in which all or a portion of the polyhedrin gene was deleted makes advantageous use of the facts (1) that no polyhedrin will be produced by these viruses and (2) the non-occluded (lacking a polyhedrin coat) form is viable and infectious in insect cell culture.

In those recombinant AcMNPV viruses in which all or a portion of the polyhedrin gene was deleted, e.g., those resulting from transfection with the preferred recombinant shuttle vectors pAc101-IFN-β, pAc311-IFN-β, pAc360-IFN-β, pAc373-IFN-β and pAc380-IFN-β, the recombinant AcMNPV viruses are isolated as follows.

The extracellular virus present in the medium at 3 days post transfection was used in a standard AcMNPV polyhedrin plaque assay described by L. E. Volkman, M. D. Summers and C. H. Hsieh, *J. Virol.* 19, 820–832 (1976). The plaques that developed were either from cells infected with nonrecombinant AcMNPV, which produced viral occlusions, or the result of cells infected with recombinant AcMNPV virus, which did not produce viral occlusions. The latter type plaque (0⁻ plaques) was initially distinguished from the former (0+ plaques) by their appearance under a low power binocular microscope. 0⁻ plaques were marked and examined with the aid of an inverted phase microscope, in which individual viral occlusions, if present, could be seen in the nucleus of the infected cells.

The virus from an $\bar{0}$ plaque was plaque purified and the DNA analyzed with the appropriate restriction enzymes to confirm that the recombinant AcMNPV vector had an insertion of the foreign gene in the proper location in EcoRI-I. No other changes were detected. Large stocks of the desired recombinant virus were then obtained by infecting susceptible insect cells using standard procedures.

EXAMPLE VI

Selection of Recombinant AcMNPV Expression Vector in Recombinants in Which the Polyhedrin Gene is Expressed In the case of those infected insect cells in which the recombinant AcMNPV viruses are those resulting from transfection with recombinant shuttle vectors in which the polyhedrin gene is intact, as discussed in Example III, the recombinant AcMNPV viruses will occur in the occluded form. Consequently, it would not be possible to distinguish them from the nonrecombinant viruses by the preferred method outlined above. Recombinants of this type could be identified among plaques produced from the progeny virus that result from the mixed transfection as follows.

The plaques that will form from recombinant AcMNPV expression vectors, i.e., have an insertion of foreign DNA into their genomes, may be distinguished from non-recombinant viral plaques using DNA restriction analysis or hybridization analysis (using a radioactively labeled DNA probe that was specific for the foreign DNA) of the viral DNA from each individual plaque. A relatively convenient procedure for detection in situ of foreign DNA in eukaryotic cells (i.e., hybridizing a labeled DNA probe to viral DNA present in plaques produced in infected animal cells) is described by Villarreal and Berg, *Science* 196, 183–186 (1977) and Hayday, et al., *Gene* 15, 53–65 (1981). This procedure has been adapted in this laboratory to detect baculovirus specific DNA sequences in baculovirus infected insect cells. It should be noted that this procedure may also be used, although not as conveniently, in lieu of the preferred procedure outlined above for the identification of 0⁻ plaques resulting from the deletion of all or a portion of the polyhedrin gene.

EXAMPLE VII

Production of β-Interferon Using AcMNPV Recombinant Expression Vector

In order to produce the desired gene product, the recombinant baculovirus must be infected in susceptible host insect cells. The following procedure was utilized for the preferred AcMNPV expression vectors formed by recombination with the recombinant shuttle vectors pAc101-IFN-β, pAc311-IFN-β, pAc360-IFN-β, pAc373-IFN-β and pAc380-IFN-β(see FIG. 5).

Susceptible *S. frugiperda* host cells were first grown either in suspension culture or in monolayers to a density of from 1 to $5\times 10^6$ cells/ml (the concentration of cells for optimal expression may vary for each different AcMNPV expression vector). The growth medium was removed and replaced with medium containing from 0.1 to 100 (optimal concentration may vary) plaque forming units of recombinant virus, e.g., Ac380-IFN-$\beta$ (FIG. 5) for about 1 hour at 23° C. The inoculum may be left on the cells or removed and replaced with the appropriate amount of fresh medium.

The protein from the cloned IFN-$\beta$ gene was produced in *S. frugiperda* cells infected with the Ac-380-IFN-$\beta$ expression vector from about 12 hours post infection (p.i.) to 3 days p.i. The entire infection process, including viral protein synthesis, viral assembly, and cell lysis was complete at about 72 hours. There was a marked reduction in protein synthesis between 50 and 60 hours p.i., and cell lysis was first detected at about 50 hours p.i. The kinetics of the expression of the IFN-gene varied depending upon the host cell and the site at which the gene was cloned into the polyhedrin gene.

The kinetics of IFN-$\beta$ expression for each of the recombinant viruses is summarized in Table 1. Significant levels of interferon were detected by 48 hours p.i. in cells infected with each of the expression vectors except Ac373-IFN-$\beta$ (Table 1). Of the expression vectors examined, Ac380-IFN-$\beta$ produced the highest titre of interferon activity (Table 1).

Intracellular levels of interferon activity were also measured and are reported in Table 1. Less than 5% of the total interferon activity remained inside Ac380IFN-$\beta$ infected cells at 48 hours p.i., demonstrating that IFN-$\beta$ secretory signals were recognized and the protein was efficiently released into the media during infection. At 12 hours p.i., the medium from Ac380-IFN-$\beta$ infected cells had about 10,000 IU/ml of interferon and increased to a maximum of nearly $5\times 10^6$ IU/ml by 42 hours p.i.

TABLE 1

The kinetics of interferon expression were examined in *S. frugiperda* cells infected with the various expression vectors. The results of these experiments were as follows:

| Viruses | Inside cell $10^6$ IU/$10^7$ cells | Outside cell $10^6$ IU/$10^7$ cells | $10^6$ IU/liter | Activity Secreted (%) |
|---|---|---|---|---|
| Ac380-IFN-$\beta$ | 0.98 | 50.7 | 5,070 | 98.1 |
| Ac360-IFN-$\beta$ | 0.96 | 20.8 | 2,080 | 95.6 |
| Ac311-IFN-$\beta$ | 0.013 | 1.4 | 140 | 99.1 |
| Ac101-IFN-$\beta$ | 0.043 | 0.007 | 0.7 | 14.0 |
| Ac373-IFN-$\beta$ | 0 | 0 | 0 | 0 |
| AcMNPV | 0 | 0 | 0 | 0 |

The synthesis of polyhedrin in AcMNPV infected cells is known to follow a similar temporal pattern of expression. Although less interferon was produced in Ac360-IFN-$\beta$ and even less in Ac311-IFN-$\beta$ virus infected cells, greater than 95% of the activity was present in the medium (Table 1). A relatively low level of interferon was detected in Ac101-IFN-$\beta$ infected cells, most of which was intracellular (Table 1).

No interferon activity and no new proteins were observed in pAc373-IFN-$\beta$ infected cells. It is not clear why the IFN-$\beta$ gene sequence inserted into the leader sequences of the polyhedrin gene was not expressed. Although sequence analysis of the shuttle vector pAc373 and extensive restriction enzyme analysis of the recombinant virus did not reveal any mutations, this explanation cannot be ruled out.

The titre of recombinant virus infected cells reached a maximum of 3 to $8\times 10^8$ plaque forming units per milliliter of medium, which is typical of AcMNPV infected cells. Thus, it appears that the insertion of the IFN-gene into the polyhedrin gene had no major effect on the replication of the virus. To test this, $2\times 10^6$ *S. frugiperda* cells were treated for 12 hours with up to $5\times 10^6$ IU/ml of interferon produced in Ac380-IFN-$\beta$ infected cell medium or $5\times 10^3$ IU/ml of an international standard of human interferon, then the treated cells were infected with 100 plaque forming units of AcMNPV or Ac380-IFN-$\beta$. Exposure of the cells to interferon had no measurable effect on the number of virus plaques that developed.

The virus plaque-reduction assay in human amnionic WISH cells challenged with vesicular stomatitis virus was used to assay for interferon activity. If virus particles were removed by centrifugation, no interferon activity was measured in medium from AcMNPV infected cells. However, if AcMNPV virus-containing media was used during interferon assays, 1000 to 3000 international reference units (IU)/ml of interferon were produced, indicating that AcMNPV virions apparently induced endogeonous interferon in WISH cells. Because many species of enveloped viruses are known to induce interferon production in human cells, these results were expected. To avoid this effect, all subsequent samples were centrifuged before testing.

We also conducted an experiment to determine whether the serum albumin (6 mg/ml) and calf serum (10%) present in the medium (see W. F. Hink, *Nature (London)* 226, 466–467 (1970)) were required for the expression of IFN- in *S. frugiperda* cells infected with Ac380-IFN-$\beta$. At 8 hours p.i., the medium was replaced with Grace's medium (no serum albumin, see T. C. C. Grace, *Nature (London)* 195, 788–789 (1962)) containing 0 to 10% fetal bovine serum. Each of the modified media were assayed for interferon activity at 48 hours p.i. Without serum, there was about a 10 fold reduction in interferon activity. With the addition of 0.5% serum, the same level of activity was produced as in controls containing 10% serum. The specific activity of IFN-$\beta$ in Ac380-IFN-$\beta$ infected cells was about $5\times 10^6$ IU/mg of protein when produced in Grace's medium containing 0.5% serum. Assuming that the activity of purified $\beta$-interferon is $5\times 10^8$ IU/ml (see E. Knight, Jr., *Proc. Natl. Acad. Sci. U.S.A.* 73, 520–523 (1976)), $\beta$-interferon would represent about 1% of the total protein in the medium.

It is understood that the invention and the advantages and opportunities presented by it will be recognized from the above description, which merely describes several preferred embodiments of the invention. It is apparent that many changes in the materials, methods and amounts of materials utilized may be made without departing from the scope and spirit of the invention or compromising any of its advantages. Further, it will be recognized that the above-described invention has uses which are predicated on making advantageous use of the fact that the present invention may be utilized to insert any gene at any of several locations in a baculovirus genome.

For instance, the fact that procedures are available for the isolation of recombinant AcMNPV viruses in which all or a portion of the polyhedrin gene has not been deleted makes it possible to utilize the present invention in a number of ways. These uses may take advantage of the fact that the polyhedrin coating of the occluded form of the AcMNPV virus is so resistant to external influences. For instance, as discussed in Example III, a selected gene could be cloned into the viral genome at a location other than in the polyhedrin gene, in particular at a location such that expression of the selected gene would be controlled by the 10K promoter so that it would be expressed at high levels. This recombinant AcMNPV virus could then be isolated and utilized as a stable expression vector.

Such a stable expression vector might be utilized as a stable form in which a recombinant AcMNPV virus could be transferred, along with a culture of the appropriate host cells and sufficient media, from one laboratory to another for eventual use in the production of a desired protein at some designated time in the future.

The expression vector might also be used in a system for controlling pest insect populations by selecting a gene which produces a protein which is toxic to a specific host insect species or a broad spectrum of susceptible host insect species and cloning that gene into the AcMNPV expression vector (these possibilities are discussed by L. K. Miller, et al., *Science* 219, 715–721 (1983), hereby incorporated by reference). The recombinant expression vector could be applied to the plant or animal upon which the insect(s) is a pest, and when it is ingested by the pest insect(s), as discussed above, the occlusion will dissociate in the lumen of the intestine, the recombinant virus will invade the cells of the intestinal wall and begin replication.

During replication, the gene for the protein toxic to the pest insect will be expressed, resulting in the death of the insect in a much shorter period than if the insect had ingested the wild type AcMNPV virus, in which case the insect would by lysed after a period which would vary depending upon the extent of the viral infection. Indications from experiments in this and other laboratories are that expression of the 10K protein occurs as early as 24 hours post infection and at high levels at about 48 hours, consequently, a gene encoding for a desired insect toxin which is cloned into the AcMNPV genome under the control of the 10K promoter would also be expected to be expressed according to that time schedule. The death of the insect could be expected soon after the initiation of expression of that selected gene, resulting in a concomitant decrease in damage to the plants or animals upon which that pest insect preys as compared to an infection of the insect with the wild-type baculovirus.

The gene could also be inserted into the baculovirus genome so that it was fused to the polyhedrin structural sequence in such a way that when the polyhedrin coating is dissociated by the alkaline conditions of the insect gut, the toxic gene product would be released. Such a use of the present invention would result in the poisoning of the insect(s) without expression of the recombinant gene in the insect intestinal cells.

Further, it will be recognized that even higher levels of gene expression than those measured in the above-described examples are possible utilizing the present invention. For instance, the IFN-β gene (or any other gene) could be cloned into the baculovirus genome more than once. In particular, copies could be inserted so that expression is under control of the polyhedrin promoter, other copies could be inserted so that expression is under control of the 10K promoter, and then several more copies could be inserted at various other restriction sites, each copy including either its own promoter or some other DNA sequence recognized by the baculovirus as a promoter. Upon infection into susceptible insect cells, the amount of interferon (or other polypeptide) produced could be vastly increased over the levels measured above.

Further modifications of the invention herein disclosed will occur to persons skilled in the art who have the benefit of this disclosure, and all such modifications are deemed to be within the spirit and scope of the invention as defined by the appended claims.

What is claimed is:

1. A method for producing a recombinant baculovirus expression vector, capable of expressing a selected heterologous gene in a host insect cell, comprising:
    (a) cleaving baculovirus DNA to produce a DNA fragment comprising a polyhedrin promoter and sufficient flanking DNA sequences to facilitate homologous recombination;
    (b) preparing a recombinant shuttle vector by inserting said DNA fragment into a cloning vehicle and thereafter inserting at least one selected heterologous gene into the thus modified cloning vehicle such that said selected heterologous gene is under the transcriptional control of the baculovirus promoter;
    (c) contacting said recombinant shuttle vector with baculovirus DNA so as to effect recombination, thereby producing a mixture of recombinant and nonrecombinant baculoviruses; and
    (d) isolating a recombinant baculovirus expression vector from said mixture.

2. The method of claim 1 wherein the baculovirus is *Autographa californica* MNPV, *Trichoplusia ni* MNPV, *Rachiplusia ou* MNPV or *Galleria mellonella* MNPV.

3. The method of claim 1 wherein the baculovirus is *Autographa californica* MNPV.

4. A method for producing a baculovirus shuttle vector, capable of being utilized as an intermediate vehicle for the genetic manipulation of a baculovirus genome, which comprises:
    (a) cleaving baculovirus DNA to produce a DNA fragment comprising a polyhedrin promoter and sufficient flanking DNA sequence to facilitate homologous recombination;
    (b) inserting said baculovirus DNA fragment into a cloning vehicle to form a modified cloning vector;
    (c) identifying a selected restriction site of the cloned baculovirus DNA fragment which is under the transcriptional control of the polyhedrin promoter; and
    (d) creating a shuttle vector by deleting from the modified cloning vector the additional restriction sites identical to the identified selected restriction site so as to create a unique restriction site in the baculovirus DNA fragment under the transcriptional control of the polyhedrin promoter.

5. The method of claim 4 wherein the baculovirus is *Autographa californica* MNPV, *Trichoplusia ni* MNPV, *Rachiplusia ou* MNPV or *Galleria mellonella* MNPV.

6. The method of claim 4 wherein the baculovirus is *Autographa californica* MNPV.

7. The method of claim 4 which further comprises the step of inserting a selected heterologous gene into the shuttle vector such that said selected heterologous gene is under the transcriptional control of said polyhedrin promoter.

8. A method for synthesizing a selected polypeptide which comprises infecting a susceptible host insect cell with a recombinant baculovirus expression vector wherein said expression vector is a recombinant baculovirus genome comprising at least one selected heterologous polypeptide structural gene under the transcriptional control of a baculovirus polyhedrin promoter.

9. The method of claim 8 wherein the baculovirus is *Autographa californica* MNPV, *Trichoplusia ni* MNPV, *Rachiplusia ou* MNPV or *Galleria mellonella* MNPV.

10. The method of claim 8 wherein the baculovirus is *Autographa californica* MNPV.

11. A recombinant baculovirus expression vector, capable of expressing a selected heterologous gene in a host insect cell, wherein said expression vector is a baculovirus genome comprising a selected heterologous gene under the transcriptional control of a baculovirus polyhedrin promoter.

12. The recombinant baculovirus expression vector of claim 11 wherein the baculovirus promoter is derived from *Autographa californica* MNPV, *Trichoplusia ni* MNPV, *Rachiplusia ou* MNPV or *Galleria mellonella* MNPV.

13. The recombinant baculovirus expression vector of claim 11 wherein the baculovirus promoter is derived from *Autographa californica* MNPV.

14. The recombinant baculovirus expression vector of claim 11 wherein all or a portion of the DNA sequence coding for the baculovirus polyhedrin structural gene under the transcriptional control of the promoter is deleted.

15. A baculovirus shuttle vector, capable of being utilized as an intermediate vehicle for the genetic manipulation of a baculovirus genome, which comprises a cloning vehicle having a DNA sequence comprising an intact replicon capable of replication within a unicellular organism and further comprising a baculovirus polyhedrin promoter and sufficient flanking baculovirus DNA sequences to facilitate homologous recombination, and a unique restriction site for cloning a selected heterologous gene, said unique restriction site being located such that the selected heterologous gene will be under the transcriptional control of said baculovirus polyhedrin promoter when inserted into said unique restriction site.

16. The baculovirus shuttle vector of claim 15 wherein the DNA sequence comprises an EcoRI-I 7.3 kilobase DNA fragment of baculovirus.

17. The baculovirus shuttle vector of claim 16 wherein a unique restriction site exists at about 4210 bases downstream of the EcoRI-I origin.

18. The baculovirus shuttle vector of claim 15 wherein the unique restriction site is a BamHI site.

19. The baculovirus shuttle vector of claim 15 wherein the selected heterologous gene is inserted at the unique restriction site.

20. The baculovirus shuttle vector of claim 15 wherein all or a portion of the DNA sequence coding for the baculovirus polyhedrin structural gene under the transcriptional control of the promoter is deleted.

21. The baculovirus shuttle vector of claim 15 wherein the baculovirus promoter is derived from *Autographa californica* MNPV, *Trichoplusia ni* MNPV, *Rachiplusia ou* MNPV or *Galleria mellonella* MNPV.

22. The baculovirus shuttle vector of claim 15 wherein the baculovirus promoter is derived from *Autographa californica* MNPV.

23. A method for producing a recombinant baculovirus expression vector capable of expressing a selected gene in a host insect cell, comprising:
  (a) cleaving baculovirus DNA to produce a DNA fragment comprising a baculovirus polyhedrin promoter, and sufficient flanking DNA sequences to facilitate homologous recombination;
  (b) inserting said baculovirus DNA fragment into a cloning vehicle to form a modified cloning vector;
  (c) identifying a selected restriction site of the cloned baculovirus DNA fragment which is under the transcriptional control of the baculovirus polyhedrin promoter;
  (d) deleting from the modified cloning vector the additional restriction sites identical to the identified selected restriction site so as to create a unique restriction site in the baculovirus DNA fragment under the transcriptional control of the baculovirus polyhedrin promoter;
  (e) inserting a selected heterologous gene into said unique restriction site to form a recombinant shuttle vector;
  (f) contacting said baculovirus shuttle vector with baculovirus DNA so as to effect recombination, thereby producing a mixture of recombinant and nonrecombinant baculoviruses; and
  (g) isolating a recombinant baculovirus expression vector from said mixture.

24. The method of claim 23 wherein the baculovirus is *Autographa californica* MNPV, *Trichoplusia ni* MNPV, *Rachiplusia ou* or *Galleria mellonella* MNPV.

25. The method of claim 23 wherein the baculovirus is *Autographa californica* MNPV.

26. The method of claim 23 wherein the DNA fragment is an EcoRI-I 7.3 kilobase DNA fragment of baculovirus.

27. The method of claim 26 wherein the unique restriction site of the cloned EcoRI-I fragment is between about 4000 and 4120 bases downstream of the EcoRI-I origin.

28. The method of claim 23 which further comprises in step (d), deleting baculovirus DNA comprising all or a portion of the structural gene sequence under the transcription control of the polyhedrin promoter.

29. The method of claim 23 wherein the unique restriction site is a BamHI site.

* * * * *